(12) United States Patent
Lourdhusamy et al.

(10) Patent No.: US 7,739,924 B2
(45) Date of Patent: Jun. 22, 2010

(54) SENSOR ASSEMBLY HAVING A FLOW HEAD

(75) Inventors: Anthoniraj Lourdhusamy, West Jordan, UT (US); Balakrishnan G. Nair, Sandy, UT (US)

(73) Assignee: Caterpillar Inc., Peoria, IL (US)

( * ) Notice: Subject to any disclaimer, the term of this patent is extended or adjusted under 35 U.S.C. 154(b) by 11 days.

(21) Appl. No.: 12/071,892

(22) Filed: Feb. 27, 2008

(65) Prior Publication Data

US 2009/0211333 A1  Aug. 27, 2009

(51) Int. Cl.
*G01N 1/00* (2006.01)
(52) U.S. Cl. .......................... 73/863; 73/23.2; 73/31.05
(58) Field of Classification Search ................... 73/863, 73/23.2, 31.05
See application file for complete search history.

(56) References Cited

U.S. PATENT DOCUMENTS

| | | | |
|---|---|---|---|
| 4,177,125 | A | 12/1979 | Barnabe |
| 4,875,990 | A | 10/1989 | Kodachi et al. |
| 4,944,861 | A | 7/1990 | Reber |
| 5,296,112 | A | 3/1994 | Seger et al. |
| 5,389,223 | A | 2/1995 | Hoetzel |
| 5,614,658 | A | 3/1997 | Moss |
| 5,711,863 | A | 1/1998 | Henkelmann et al. |
| 6,015,533 | A | 1/2000 | Young et al. |
| 6,296,748 | B1 | 10/2001 | Ohtsuki et al. |
| 6,348,141 | B1 | 2/2002 | Kato et al. |
| 6,409,899 | B1 | 6/2002 | Satou et al. |
| 6,585,872 | B2 | 7/2003 | Donelon et al. |
| 7,217,355 | B2 | 5/2007 | Nair et al. |
| 2004/0011645 | A1 | 1/2004 | Beckmeyer et al. |
| 2004/0144645 | A1 | 7/2004 | Yamada et al. |
| 2005/0016849 | A1 | 1/2005 | Ikoma et al. |
| 2007/0012566 | A1 | 1/2007 | Nair et al. |
| 2007/0246359 | A1 | 10/2007 | Sugiyama et al. |
| 2007/0261473 | A1 | 11/2007 | Weyl et al. |
| 2008/0017510 | A1 | 1/2008 | Nair et al. |

FOREIGN PATENT DOCUMENTS

| | | |
|---|---|---|
| JP | 2004279267 | 10/2004 |
| KR | 1020000064981 | 11/2000 |
| KR | 1020040089711 | 10/2004 |

*Primary Examiner*—Daniel S Larkin
*Assistant Examiner*—Rodney T Frank
(74) *Attorney, Agent, or Firm*—Finnegan, Henderson, Farabow, Garrett & Dunner

(57) ABSTRACT

A flow head for a gas sensor having a sensing element is provided. The flow head includes a body at least partially defining a cavity in thermal communication with the sensing element. The body includes an inlet port located within an annular surface of the body and an outlet port located within the annular surface of the body. The body also includes an inlet passage offset from and parallel to the cavity, wherein the inlet passage configures the inlet port and the cavity to be in fluid communication with one another. The body further includes an outlet passage offset from and parallel to the cavity, wherein the outlet passage configures the outlet port and the cavity to be in fluid communication with one another.

16 Claims, 2 Drawing Sheets

SENSOR ASSEMBLY HAVING A FLOW HEAD

TECHNICAL FIELD

The present disclosure relates generally to a sensor assembly, and more particularly, to a sensor assembly having a flow head.

BACKGROUND

The composition of exhaust produced by the combustion of hydrocarbon fuels is a complex mixture of oxide gases (NOX, $SO_X$, $CO_2$, CO, $H_2O$), unburned hydrocarbons, and oxygen. Measurement of the concentration of these individual exhaust gas constituents in real time can result in improved combustion efficiency and lower emissions of polluting gases. Various devices have been proposed to operate as exhaust gas sensors that have the capability of measuring the concentration of a gas constituent in an exhaust stream. Many of these devices require the flow inside the sensor to be regulated and/or maintained within a certain allowable range. In order to help ensure accuracy of the devices, the sampling conditions of the exhaust gas should be precisely controlled.

The sampling conditions can include a sampling rate and/or an amount of gas flow provided to a sensing element. For example, a low exhaust pressure external to the sensing element may hinder the necessary amount of gas from contacting the sensing element. Also, the flow of exhaust gas monitored by such sensors typically has pulsations in its flow rate caused at least in part by engine cylinder firings. These pulsations have been shown to result in measurement error. Furthermore, a catalyst structure may also be employed to improve sampling conditions by converting one or more constituents into another constituent prior to measuring the constituents.

One method of regulating the flow of exhaust through a gas sensor is described in U.S. Pat. No. 6,015,533 (the '533 patent) issued to Young et al. on Jan. 18, 2000. Specifically, the '533 patent discloses a cylindrical sensor housing having an inner shroud and an outer shroud that directs the flow of exhaust into and out of the sensor housing. Gas flows into the sensor housing via orifices located within cylindrical walls, at a tip end of the outer shroud. The gas then travels through gas channels running longitudinally, with respect to the cylinder walls, between the inner shroud and the outer shroud. At a proximal end of the inner shroud, the gas passes through a diffuser, reverses direction, and passes through a chamber defined by the inner shroud and a sensing device. The gas then passes over a tip end of the sensing device and out of the sensor housing via a port located at a distal end of the outer shroud, substantially perpendicular to the orifices.

Although the sensor housing of the '533 patent may suitably regulate gas flow through a sensor, the sensor design may have some limitations. Specifically, the complexity of the sensor may increase the costs associated with manufacturing and distribution of the sensor. The presence of the diffuser may render the sensor susceptible to clogging due to soot present in the exhaust. And, the diffuser may be difficult to access and therefore costly to service and/or replace. Furthermore, the '533 patent includes, nor allows for, a catalyst structure to filter and/or condition the exhaust prior to the exhaust contacting the sensing device. This may hinder the reliability of the readings acquired by the sensing device.

SUMMARY OF THE DISCLOSURE

In one aspect, the present disclosure is directed to a flow head for a gas sensor having a sensing element. The flow head may include a body at least partially defining a cavity in communication with the sensing element. The body may include an inlet port located within an annular surface of the body and an outlet port located within the annular surface of the body. The body may also include an inlet passage offset from and parallel to the cavity, wherein the inlet passage configures the inlet port and the cavity to be in fluid communication with one another. The body may further include an outlet passage offset from and parallel to the cavity, wherein the outlet passage configures the outlet port and the cavity to be in fluid communication with one another.

In another aspect, the present disclosure is directed to a method of sampling exhaust. The method may include driving exhaust into a sampling chamber, drawing exhaust from the sampling chamber, and conditioning the exhaust as it flows into or out of the sampling chamber.

DETAILED DESCRIPTION

Figure 1:
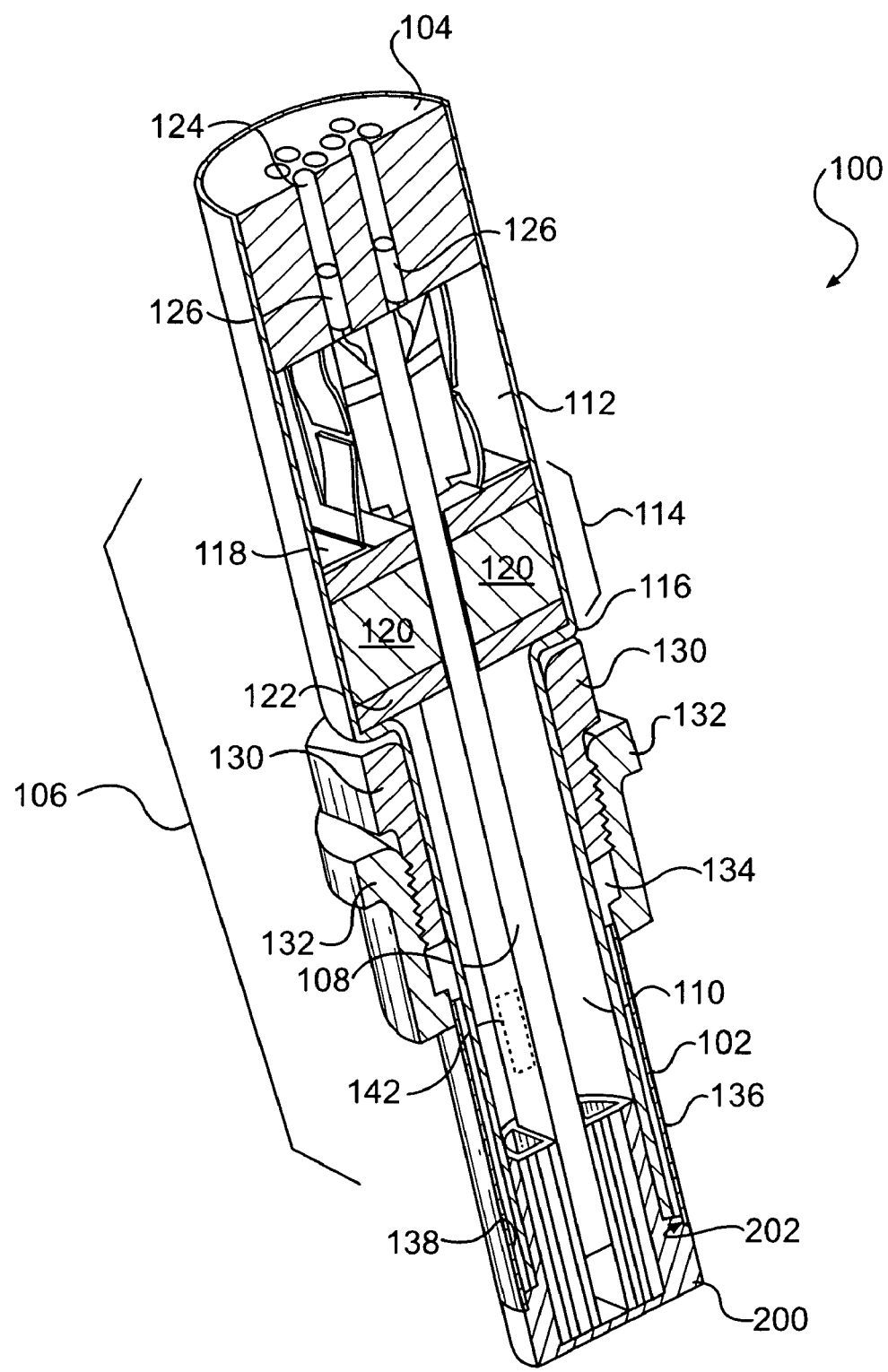
FIG. 1 is a pictorial illustration of an exemplary disclosed sensor assembly.

Referring to FIG. 1, the basic features of an exemplary disclosed sensor assembly 100 are illustrated. The sensor assembly 100 may include multiple components that cooperate to allow a gas stream such as, for example, exhaust from an engine, to be sampled and the constituents of the gas monitored. The sensor assembly 100 may include a housing 102 configured to receive a grommet 104 at one end and a flow head 200 at an opposing end. The housing 102, grommet 104, and flow head 200 may, together, substantially form an enclosure 106. A sensing element 108 may be disposed within the enclosure 106 and extend from the flow head 200 toward the grommet 104.

The enclosure 106 may be divided into a sampling chamber 110 and a sealed chamber 112 by disposing a sealing assembly 114 within the housing 102. The sealing assembly 114 may be secured within the housing 102 in any manner known in the art. For example, as shown in FIG. 1, the housing 102 may have a stepped portion 116, against which the sealing assembly 114 may be seated. The stepped portion 116 may inhibit the sealing assembly 114 from displacing toward the flow head 200, and a metal ring 118 may inhibit the sealing assembly from displacing toward the grommet 104.

The sensing element 108 may pass through a center portion of the sealing assembly 114. The sealing assembly 114 may be comprised of a ceramic seal 120 sandwiched between two rings 122. The materials of the ceramic seal 120 and the rings 122 may differ. In one example, the ceramic seal 120 may be a compacted powder, whereas the rings 122 may be fabricated from a solid ceramic. In the aforementioned example, the ceramic seal 120 and ring 122 may be crimped together, thereby compressing the ceramic seal 120 around the sensing element 108 and against the housing 102 to form a seal between the sampling chamber 110 and the sealed chambers 112. It is contemplated that alternative methods may be known in the art and used to form a seal around sensing element 108, if desired.

The grommet 104 may be formed from a high temperature resistant material such as, for example, Viton®, Polytetrafluoroethylene (PTFE), or any other heat resistant polymer known in the art. The grommet 104 may have at least one passage 124 disposed therein to allow electrical leads to pass therethrough and connect to at least one terminal 126 in communication with sensing element 108. Terminal 126 may be used to communicate signals from sensing element 108 to an external controller (not shown). Additionally, it is contemplated that passage 124 may facilitate the supply of electrical power to one or more components of the sensing element 108 such as, for example, heating elements and/or temperature sensors (both not shown), if desired.

The sensor assembly 100 may also include a mounting arrangement used to attach the housing 102 to an exhaust passage extending from an engine. As illustrated in FIG. 1, the arrangement may include a spin nut 130 and a boss 132. The boss 132 may have an opening that allows the housing 102 to pass therethrough, and may be permanently secured to the exhaust passage in any manner known in the art such as, for example, by welding. The spin nut 130 may be configured to rotate around the housing 102 and threadingly engage the boss 132. As the spin nut 130 is threaded into the boss 132, the spin nut 130 may press an annular ring 134 fixed to the housing 102 against a lip within the boss 132. Thus, the sensor assembly 100 may be secured to the exhaust passage with the flow head extending into the exhaust passage. It is contemplated that a seal may be placed between the annular ring 134 and the boss 132 to inhibit gas leakage, if desired.

Sensing element 108 may be a mixed potential gas sensor configured to determine the level of one or more constituents within an exhaust stream. Sensing element 108 may be composed of one or more substrate layers and one or more sensing electrodes connected to the substrate layers and the terminals 126. Sensing element 108 may also be composed of one or more heating elements 142 configured to maintain the sensing electrodes at a predetermined temperature.

As also shown in FIG. 1, one end of the sensing element 108 may extend at least partially into the flow head 200. The flow head 200 may include a body 201 having a stepped exterior portion 202 (shown in FIG. 2) which seats against an end of the housing 102. The stepped portion 202 may also seat against an end of an insulation sleeve 136 surrounding a portion of the housing 102, between the boss 132 and the flow head 200. Insulating sleeve 136 may help insulate sensing element 108 from the heat of an exhaust flow. A gap 138 may be formed between housing 102 and insulating sleeve 136 to help insulate sensing element 108 from the heat of an exhaust flow.

Figure 2:
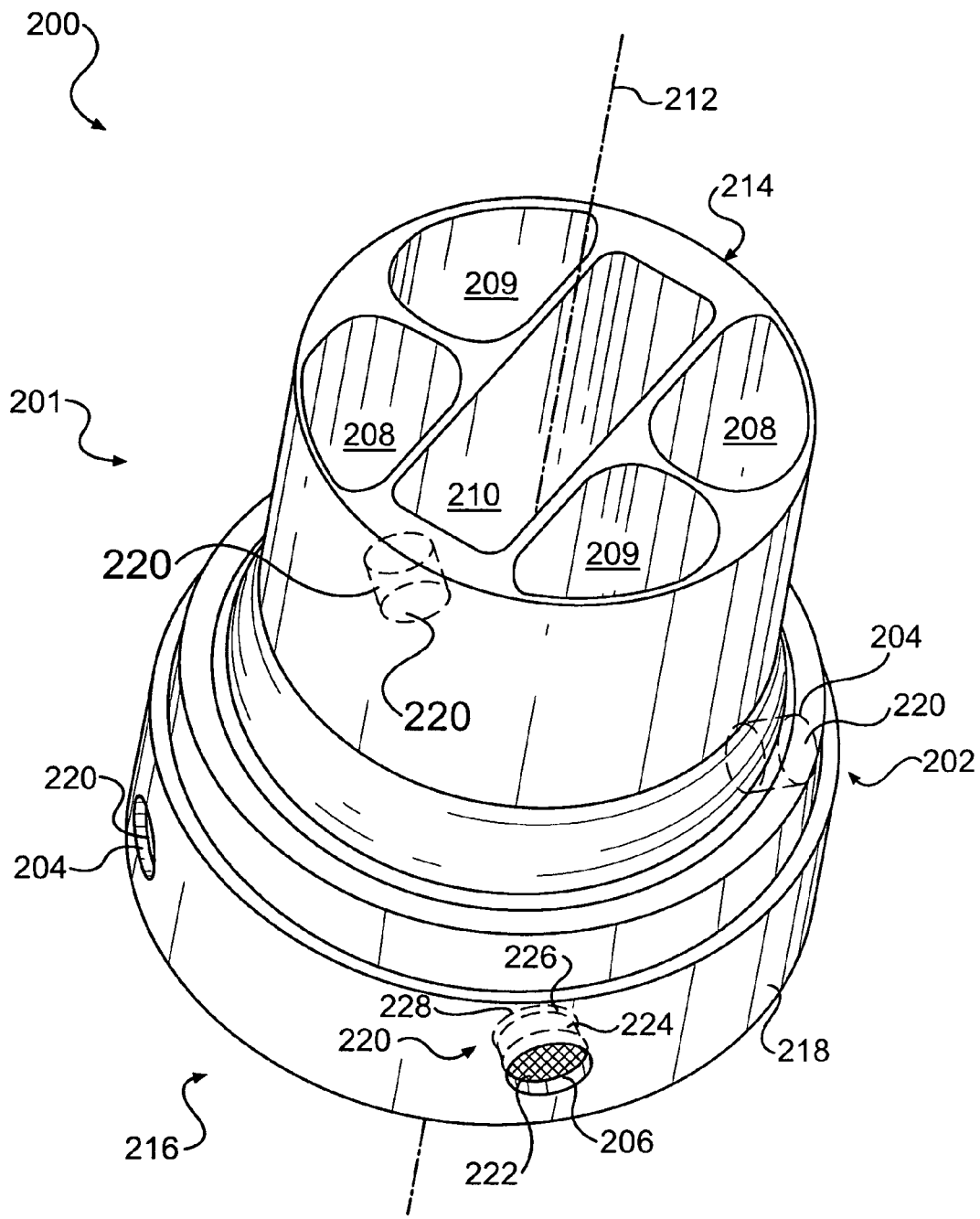
FIG. 2 is a pictorial illustration of an exemplary disclosed flow head that may be used with the sensor assembly of FIG. 1.

As shown in FIG. 2, the flow head 200 may also include at least one inlet port 204 and at least one outlet port 206 configured to direct a portion of an exhaust flow into and out of the sampling chamber 110. In one embodiment, flow head 200 includes two inlet ports 204 and two outlet ports 206 disposed adjacent to each other at right angles around an annular surface 218 of the body 201. An inlet passage 208 and an outlet passage 209 may facilitate fluid communication between each of the inlet and outlet ports 204, 206 and the sampling chamber 110. In particular, each inlet port 204 may communicate with the sampling chamber 110 via an inlet passage 208, while each outlet port 206 may communicate with the sampling chamber 110 via an outlet passage 209. Additionally, the flow head 200 may have a cavity 210 configured to secure and thermally communicate with the sensing element 108. That is, the heating element disposed within the sensing element 108 may heat the flow head 200 as the sensing element 108 is being heated.

Flow head 200 may be fabricated, for example, by machining, investment casing, powder metallurgy or other typical metal fabrication processes. Alternate embodiments of flow head 200 may be fabricated through low cost, high volume metal manufacturing processes such as deep-drawing or stamping A catalyst assembly 220 may be disposed within any one or more of the inlet and outlet ports 204, 206. In one example, catalyst assembly 220 may be an oxidation catalyst that converts NO to $NO_2$. In another example, the same or a different catalyst assembly 220 may function to oxidize solid particles such as $CH_4$, CO, etc., and/or remove potential contaminants such as $SO_2$.

Catalyst assembly 220 may be fabricated by inserting stainless steel tubing into the respective ports 204, 206, and installing a metallic mesh plug 222, for example, by press fitting the plug, into the end of the tubing. However, it is contemplated that the catalyst assembly 220 may be fabricated directly inside of the inlet and/or outlet ports 204, 206 without the tubing, if desired. An active material such as a catalyst, filter, flow restrictor or absorber material may be inserted into the tubing adjacent the plug 222. Another metallic mesh screen 228 may be secured such as, for example, by spot-welding, to the down-stream side of the tubing to secure the active material. The active material may have one or more stages each of which could be a catalyst, filter, flow restrictor or absorber material. In one example, the active material may have two stages, one being an absorber material 224, such as calcium oxide (CaO), and another being an oxidizing catalyst material 226, such as Pt-loaded γ-alumina, in the form of pellets.

In the aforementioned example, the CaO powder 224 may be inserted into the stainless steel tubing and lightly compacted using a rod to press the powder 224 against the surface of silver mesh plug 222. Next, the Pt-loaded γ-alumina pellets 226 may be inserted into the tubing, and again a rod may be used to lightly compact the pellets 226 against the CaO powder 224. Finally, a nickel mesh screen 228 may be spot welded to the tubing against the pellets 226 to keep the powder 224 and pellets 226 in place. While the aforementioned example describes a two stage catalyst assembly 220, it is contemplated that any number of stages may be used with alternative materials, if desired.

An axis 212 may pass through a center of the flow head 200, from a proximal end 214 to a distal end 216. The inlet and outlet ports 204, 206 may be aligned substantially perpendicular to the axis 212 and the annular surface 218 of the flow head 200. The inlet and outlet passages 208, 209 may be generally parallel to the axis 212. The inlet and outlet ports 204, 206 may be evenly spaced apart along the annular surface 218.

The cross-sectional areas of the inlet and outlet ports 204, 206 may vary according to a desired function of the flow head. That is, as the flow head is immersed in a flow of fluid, such as an exhaust stream, the orientation of the inlet and outlet ports 204, 206, in conjunction with the passages 208, 209 and the sampling chamber 110, may create a pressure differential between the inlet ports 204 and the outlet ports 208. This pressure differential, driven by stagnation pressure, static pressure, and/or a Venturi effect, may cause a portion of the exhaust to be driven into the sampling chamber 110 via the inlet port 204 and the inlet passage 208. This pressure differential may also draw exhaust from the sampling chamber 110 back into the exhaust stream via the outlet port 206 and the outlet passage 209.

The inlet and outlet ports 204, 206 may be defined as inlets or outlets by their relative orientation in a gas stream. That is, in one example having two inlet ports 204 and two outlet ports 206, the inlet ports 204 may either be located adjacent or opposite each other. For example, when the flow head 200 is positioned in a gas stream such that two ports are substantially inline with the gas stream and two ports are substantially perpendicular to the gas stream, the two inline ports may function as the inlet ports 204, while the two substantially perpendicular ports may function as the outlet ports 206. In another example, should the flow head 200 be rotated such that no ports are aligned parallel to the gas flow, the two substantially upstream ports may function as the inlet ports 204, while the other two substantially downstream ports may function as the outlet ports 206.

INDUSTRIAL APPLICABILITY

The presently disclosed sensor assembly may find potential application anywhere it is desirable to measure the constituents of a fluid. However, the presently disclosed sensor assembly may be most beneficial in measuring the constituents in an exhaust stream. The design of the disclosed flow head may allow a portion of the exhaust stream to be sampled efficiently, reliably, and economically by creating a pressure differential between one or more inlet ports and one or more outlet ports that drives exhaust into and draws exhaust out of the sensor assembly. The operation of sensor assembly 100 will now be explained.

As a flow of exhaust from an engine contacts the flow head 200, a portion of the exhaust may be driven into the sampling chamber 110 via inlet ports 204. Simultaneously, the exhaust may be drawn out of the sampling chamber 110 and back into the exhaust stream via the outlet ports 206 creating a flushing effect in the sampling chamber 110. The exhaust may be driven into the flow head 200 by stagnation pressure, while the Venturi effect may draw the exhaust out of the flow head 200.

As the exhaust flows through the sampling chamber 110, catalyst assembly 220 may condition the exhaust. That is, as the exhaust flows into the sampling chamber 110 it must pass through the catalyst assembly 220 disposed within the inlet ports 204. The catalyst assembly 220 may also be disposed in outlet ports 206 allowing sensor assembly 100 to be rotated about axis 212 without hindering the functionality of the sensor assembly 100. Because the sensing element 108 may be in thermal contact with the flow head 200, the catalyst assembly 220 may benefit from heat transferred from the sensing element 108 to the flow head 200. While the exhaust passes through the flow head 200, the exhaust may also be sampled by the sensing element 108. That is, the portion of the exhaust from the engine that is driven into the flow head 200 may be measured by sensing element 108, and a signal indication of a level of one or more constituents may be communicated to the controller by way of terminal 126.

The simplistic design of the flow head 200 may decrease manufacturing costs and improve functionality and reliability, because few moving parts are needed for the flow head 200 to function. This may also make the sensor assembly 100 cheaper to operate, because little power is needed to drive the sampling of exhaust. Additionally, the pressure differentials created by the exhaust stream and inlet and outlet ports 204, 206 may help regulate the sampling rate and ensure sensing element 108 receives a necessary amount of exhaust to sample.

It will be apparent to those skilled in the art that various modifications and variations can be made to the sensor assembly of the present disclosure. Other embodiments will be apparent to those skilled in the art from consideration of the specification and practice of the disclosed sensor assembly. It is intended that the specification and examples be considered as exemplary only, with a true scope being indicated by the following claims and their equivalents.

What is claimed is:

1. A flow head for a gas sensor having a sensing element, comprising:
    a body at least partially defining a cavity in thermal communication with the sensing element, and including:
        an inlet port defined within an annular surface of the body;
        an outlet port defined within the annular surface of the body;
        an inlet passage offset from and parallel to the cavity, wherein the inlet passage configures the inlet port and the cavity to be in fluid communication with one another; and
        an outlet passage offset from and parallel to the cavity, wherein the outlet passage configures the outlet port and the cavity to be in fluid communication with one another.

2. The flow head of claim 1, wherein the inlet and outlet ports are substantially perpendicular to the inlet and outlet passages.

3. The flow head of claim 1, wherein the inlet and outlet ports are cylindrical ports.

4. The flow head of claim 1, wherein the cavity is configured to at least partially receive the sensing element.

5. The flow head of claim 4, wherein the cavity is heated by the sensing element.

6. The flow head of claim 5, further including a catalyst assembly disposed within at least one of the inlet port and the outlet port, wherein the catalyst assembly is in thermal contact with the body.

7. The flow head of claim 6, wherein the catalyst assembly includes multiple stages.

8. The flow head of claim 1, wherein:
    the inlet port is a first inlet port;
    the outlet port is a first outlet port;
    the inlet passage is a first inlet passage in communication with the first inlet port;
    the outlet passage is a first outlet passage in communication with the first outlet port; and
    the flow head further includes:
    a second inlet port;
    a second outlet port;
    a second inlet passage in fluid communication with the second inlet port; and
    a second outlet passage in fluid communication with the second outlet port.

9. The flow head of claim 8, wherein the inlet port is substantially identical in geometry to the outlet port, and the function of the inlet port is different from the function of the outlet port due to the location relative to the exhaust flow.

10. The flow head of claim 8, wherein the inlet ports are inline with the flow of exhaust and the outlet ports are perpendicular to the flow of exhaust.

11. The flow head of claim 8, wherein the inlet ports are substantially upstream and the outlet ports are substantially downstream, relative to the flow of exhaust.

12. The flow head of claim 1, wherein the inlet port and the outlet port are evenly spaced about the annular surface of the body.

13. A gas sensor, comprising:
    a sensing element;
    a heating element disposed proximal the sensing element;
    a housing configured to at least partially surround the sensing and heating elements; and a flow head connected to the housing to at least partially define a sampling chamber, the flow head comprising;

a body configured to receive the sensing and heating elements;

an inlet port located within an annular surface of the body;

an outlet port located within the annular surface of the body;

an inlet passage offset from and parallel to the cavity, wherein the inlet passage configures the inlet port and the cavity to be in fluid communication with one another; and an outlet passage offset from and parallel to the cavity, wherein the outlet passage configures the outlet port and the cavity to be in fluid communication with one another.

14. The gas sensor of claim 13, further including a catalyst assembly disposed within at least one of the inlet port and the outlet port, wherein the catalyst assembly includes one or more stages and the catalyst assembly is in thermal contact with the body which is in thermal communication with the sensing element.

15. The gas sensor of claim 13, wherein:

the inlet port is a first inlet port;

the outlet port is a first outlet port;

the inlet passage is a first inlet passage in communication with the first inlet port;

the outlet passage is a first outlet passage in communication with the first outlet port; and the flow head further includes:

a second inlet port;

a second outlet port;

a second inlet passage in fluid communication with the second inlet port; and a second outlet passage in fluid communication with the second outlet port.

16. The gas sensor of claim 15, wherein the inlet port is substantially identical in geometry to the outlet port, and the function of the inlet port is different from the function of the outlet port due to the location relative to the exhaust flow.

* * * * *